(12) United States Patent
Auvray et al.

(10) Patent No.: US 10,825,257 B2
(45) Date of Patent: Nov. 3, 2020

(54) SYNTHETIC REPRESENTATION OF A VASCULAR STRUCTURE

(71) Applicant: KONINKLIJKE PHILIPS N.V., Eindhoven (NL)

(72) Inventors: Vincent Maurice André Auvray, Meudon (FR); Romane Isabelle Marie-Bernard Gauriau, Paris (FR); Raoul Florent, Ville d'Avray (FR); Alexandra Groth, Hamburg (DE); Juergen Weese, Norderstedt (DE)

(73) Assignee: KONINKLIJKLE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/066,736

(22) PCT Filed: Dec. 29, 2016

(86) PCT No.: PCT/EP2016/082870
§ 371 (c)(1),
(2) Date: Jun. 28, 2018

(87) PCT Pub. No.: WO2017/114916
PCT Pub. Date: Jul. 6, 2017

(65) Prior Publication Data
US 2019/0005737 A1      Jan. 3, 2019

(30) Foreign Application Priority Data
Dec. 30, 2015   (EP) ..................................... 15307182

(51) Int. Cl.
*G06T 19/00*        (2011.01)
*G06T 19/20*        (2011.01)
(Continued)

(52) U.S. Cl.
CPC .............. *G06T 19/20* (2013.01); *A61B 6/504* (2013.01); *G06T 7/30* (2017.01); *G06T 11/008* (2013.01);
(Continued)

(58) Field of Classification Search
CPC ....... G06T 19/20; G06T 11/008; A61B 6/504; G16H 15/00
See application file for complete search history.

(56) References Cited

U.S. PATENT DOCUMENTS

2003/0031351 A1*   2/2003   Yim ....................... G06K 9/342
                                                                382/130
2005/0147283 A1*   7/2005   Dwyer .................. G06T 7/0012
                                                                382/128
(Continued)

OTHER PUBLICATIONS

Schoonenberg, Gert et al "Projection based motion Compensation and Reconstruction of Coronary Segments and Cardiac Implantable Devices using Rotational X-Ray Angiography", Medical Image Analysis, vol. 13, Issue 5, Oct. 2009, pp. 785-792.
(Continued)

*Primary Examiner* — Martin Mushambo

(57) ABSTRACT

The present invention relates to an apparatus for providing a synthetic representation of a vascular structure. It is described to provide (210) at least one 2D X-ray image comprising 2D X-ray image data of a vascular structure of a patient's body part is provided. A 3D model of the body part is provided (220), the 3D model comprising a 3D modelled vascular structure. A 2D projection of the 3D model of the body part is determined (230), the 2D projection of the 3D model of the body part comprising a 2D projection of the 3D modelled vascular structure. The 3D model of the body part is transformed (240). The transform of the 3D model of the body part comprises a determination of the pose of the 3D model of the body part such that a 2D
(Continued)

projection of the 3D modelled vascular structure associated with the transformed 3D model of the body part is representative of the 2D X-ray image data of the vascular structure of the patient's body part. A medical report is generated (250) based on information determined from the 3D model.

20 Claims, 8 Drawing Sheets

(51) Int. Cl.
G06T 7/30 (2017.01)
G16H 15/00 (2018.01)
G16H 30/20 (2018.01)
A61B 6/00 (2006.01)
G06T 11/00 (2006.01)
A61B 90/00 (2016.01)

(52) U.S. Cl.
CPC ............. *G16H 15/00* (2018.01); *G16H 30/20* (2018.01); *A61B 2090/367* (2016.02); *G06T 2207/10116* (2013.01); *G06T 2207/10124* (2013.01); *G06T 2207/30048* (2013.01); *G06T 2207/30101* (2013.01); *G06T 2210/41* (2013.01); *G06T 2219/004* (2013.01); *G06T 2219/2016* (2013.01); *G06T 2219/2021* (2013.01)

(56) References Cited

U.S. PATENT DOCUMENTS

| | | | |
|---|---|---|---|
| 2006/0050941 A1 | 3/2006 | Middleton | |
| 2006/0098010 A1* | 5/2006 | Dwyer | G06T 19/006 345/424 |
| 2006/0188139 A1 | 8/2006 | Khamene | |
| 2006/0235287 A1* | 10/2006 | Desmedt | A61B 6/12 600/407 |
| 2007/0014451 A1* | 1/2007 | Dwyer | A61F 2/06 382/128 |
| 2007/0031018 A1 | 2/2007 | Camus | |
| 2010/0098309 A1 | 4/2010 | Graessner | |
| 2013/0094749 A1 | 4/2013 | Oh | |
| 2014/0371896 A1 | 12/2014 | Landon | |
| 2015/0250438 A1 | 9/2015 | Boxkaya | |
| 2015/0254043 A1 | 9/2015 | Boxkaya | |

OTHER PUBLICATIONS

Auvray, V. et al "Improved vessel enhancement for fully automatic coronary modelling". SPIE Medical imaging 2009.
Lacroix, Romain et al, "Model-based segmentation of the left main coronary bifurcation from 2D angiograms", ISBI 2012.
Dodge, J. Theodore et al "Intrathoracic spatial location of specified coronary segments on the normal human heart. Applications in quantitative arteriography, assessment of regional risk and contraction, and anatomic display," Circulation, vol. 78, No. 5, 1988.
Jomier, Julien et al "3D/2D Model-to-Image Registration Applied to TIPS Surgery", MICCAI, 2006, pp. 662-669.
Groher, Martin et al "Deformable 2D-3D Registration of Vascular Structures in a One View Scenario", IEEE Transactions on Medical Imaging, vol. 28, No. 6, 2009.
Mollus, Sabine et al "Model-to-Image Based 2D-3D-Registration of Angiographic Data", Medical Imaging 2008, Prov. of SPIE, vol. 6914.
Bredno, Jorg et al "Algorithmic Solutions for Live Device-to-Vessel Match". Proceedings of SPIE—vol. 5370, Medical Imaging 2004: Image Processing, pp. 1486-1497.
Sanborn, Timoth A. et al, "ACC/AHA/SCAI 2014 Health Policy Statement on Structured Reporting for the Cardiac Catheterization Laboratory", Journal of the American College of Cardiology, vol. 63, Issue 23, Jun. 2014.
Innervision, Cardiac Imaging 2006.
Kita, Yasuyo et al "Real-Time Registration of 3D Cerebral Vessels to X-Ray Angiograms", ISSN 0919-6072, vol. 98, No. 103, 1998.
Mori et al: "Effective Doses in Subjects Undergoing Computed Tomography Cardiac Imaging With the 256-Multislice CT Scanner"; European Journal of Radiology 65 (2008), pp. 442-448.
U.S. Appl. No. 16/066,424, Arguments and Remarks, dated Dec. 18, 2019.
U.S. Appl. No. 16/066,424, Claims, dated Dec. 18, 2019.
U.S. Appl. No. 16/066,424. Terminal Disclaimer, dated Dec. 18, 2019.
U.S. Appl. No. 16/066,424, Final Office Action, dated Feb. 10, 2020.

* cited by examiner

SYNTHETIC REPRESENTATION OF A VASCULAR STRUCTURE

CROSS-REFERENCE TO PRIOR APPLICATIONS

This application is the U.S. National Phase application under 35 U.S.C. § 371 of International Application No. PCT/EP2016/082870, filed on Dec. 29, 2016, which claims the benefit of European Patent Application No. 15307182.4, filed on Dec. 30, 2015. These applications are hereby incorporated by reference herein.

FIELD OF THE INVENTION

The present invention relates to an apparatus for providing a synthetic representation of a vascular structure to be typically integrated in an clinical interventional report, to a medical system for providing a synthetic representation of a vascular structure to be typically integrated in an clinical interventional report, and to a method for providing a synthetic representation of a vascular structure to be typically integrated in an clinical interventional report, as well as to a computer program element and a computer readable medium.

BACKGROUND OF THE INVENTION

In vascular treatments, for example in Percutaneous Transluminal Coronary Angioplasty (PTCA) to treat cardiac stenosis, information relating to the vascular treatments is required to be provided. Important findings of the vascular treatment are documented by annotating the flattened diagram of the coronary arteries. In particular, the clinician has to describe which stenosis was treated, for instance by localizing them onto a flattened schematic graph of the coronary arteries and their severity.

US 2010/0098309A1 describes a system and method of analyzing and using volumetric data of a patient is disclosed. Volumetric data characterizing a patient is obtained using an imaging modality such as a computerized tomographic device (CT), magnetic resonance imager (MR), or other tomographic modality. The volumetric data or image slices derived from the data is compared with anatomical image or model data from an anatomical atlas so as to associate the patient data with a body structure. The anatomical association is used as a search term in a data base to retrieve information which may be useful in diagnosis or treatment of the patient.

However, the flattened schematic graph of the coronary arteries is far from the actual vascular structure as observed in an angiographic image, and as a result it is not straightforward for the clinician to match features within the angiographic image with those on the schematic graph of the coronary arteries.

SUMMARY OF THE INVENTION

It would be advantageous to have an improved technique for interpreting angiograms.

The object of the present invention is solved with the subject matter of the independent claims, wherein further embodiments are incorporated in the dependent claims. It should be noted that the following described aspects of the invention apply also for the apparatus for providing a synthetic representation of a vascular structure, the medical system for providing a synthetic representation of a vascular structure, the method for providing a synthetic representation of a vascular structure, and for the computer program element and the computer readable medium.

According to a first aspect, there is provided an apparatus for providing a synthetic representation of a vascular structure, the apparatus comprising:

an input unit; and
a processing unit;

The input unit is configured to provide at least one 2D X-ray image comprising 2D X-ray image data of a vascular structure of a patient's body part. The input unit is also configured to provide a 3D model of the body part, the 3D model comprising a 3D modelled vascular structure. The 3D model of the body part is a generic model of the body part. The processing unit is configured to determine a 2D projection of the 3D model of the body part, the 2D projection of the 3D model of the body part comprising a 2D projection of the 3D modelled vascular structure. The processing unit is also configured to transform the 3D model of the body part, wherein the transform of the 3D model of the body part comprises a determination of the pose of the 3D model of the body part such that a 2D projection of the 3D modelled vascular structure associated with the transformed 3D model of the body part is representative of the 2D X-ray image data of the vascular structure of the patient's body part. The processing unit is configured to generate a medical report based on information determined from the 3D model.

In other words, X-ray images (such as an angiogram from an angiogram sequence) can be associated with a synthetic diagram representing the vascular tree (for example the coronary tree) that is presented from a similar perspective to that applied during acquisition of the angiogram. The term "angiogram" relates to a visualization of the blood vessels of the heart region, and/or vascular structure outside of the heart, of the patient.

To put this another way, the 3D model of the body part can be transformed, such as rotated, translated, or warped, such that a 2D projection of the 3D vascular structure of the 3D model looks similar to that to the angiogram. In this way, the synthetically generated 2D vascular structure looks to have been acquired by an (imaginary) X-ray acquisition unit whose X-ray source and detector were similarly positioned relative to the patient's body part as the real X-ray source and detector were positioned when the real angiogram was taken. Then, because the 3D vascular structure in the 3D model is known, i.e., all the component parts of the vascular tree are known and can be named, the 2D synthetic projection, which can have annotations applied to the vascular structure, can enable the structure within the 2D angiogram to be more easily interpreted.

In this way, a clinician is provided with help in interpreting the global nature of various angiograms in a unified way.

The 3D model of the body part is a generic model of the body part. In other words, the model is a 3D model that can be used for different patients. This means that in using a generic 3D model of the body part, a CT image of the body part, from which a patient specific model can be developed, is not required.

In this manner, a generic 3D model of a body part can be utilised for all patients, and where the known vascular structure within the 3D model can be used to aid a clinician's interpretation of an actual angiogram. In this way, the clinician is better able to determine the direction through the heart the X-rays passed for a particular angiogram. In other words, the clinician is able to spatially orientate himself with respect to the heart when looking at the angiogram. Furthermore, because the 2D projection of the 3D modelled vascular structure is of a known structure, the clinician can easily determine the identity of parts of the vascular structure in the angiogram through reference to the 2D projection of the 3D modelled vascular structure. The clinician is able to easily identify the arteries in the angiogram by their anatomical names, through reference to the matching 2D projection of the 3D model that shows the 2D projection of the modelled vascular structure as if the 3D model of the heart had itself been subjected to X-ray analysis from the same direction as that used to acquire the angiogram. A clinician may be able to identify the branches and subsegments, however it can be cumbersome to synthesize the information gained from different angiograms into an artificial flattened diagram and utilization of the 3D model in the manner described aids this process.

The clinician is also provided with a means to help him in interpreting the 2D projection of the 3D model—the diagram. The benefit is at least twofold: he does not have to do the translation a) from image to an anatomical name and then b) from the anatomical name to the diagram. Furthermore, reprojected diagrams naturally allow to aggregate the information from different sequences (different views) into one unique model. Information can easily be gathered from different views into one structure that summarizes the findings in the final report.

In other words, the processing unit is configured to transform the 3D model, through for example rotation, translation and/or warping of the 3D model and determine a 2D projection of the 3D modelled vascular structure at each point, until the vascular structure in a 2-D projection of the model matches, or approximately matches, or at least most closely matches (i.e., is good enough visually), the vascular structure in the actually acquired angiogram—i.e., in one transformation of the 3D model its 2D projection will exhibit a best fit to the angiogram. To put this another way, the 3D model is transformed until the vascular structure in a 2D projection of the model most closely correlates with the 2-D X-ray image data of the vascular structure in the angiogram.

In this manner the 3D model can be determined (and in an example refined) such that the 2D projection of the 3D modelled vascular structure associated with the transformed 3D model of the body part correlates with the 2D X-ray image data of the vascular structure of the patient's body part.

In other words, angiographic sequences of an exam are associated with a diagram presenting the coronary tree (example of 2-D x-ray image data of the vascular structure) from a similar perspective. In this manner, instead of displaying one artificially flattened complete 2-D diagram, a complete 3-D model (including a 3-D model or diagram of the vascular structure) is used which is reprojected into a series of 2-D diagrams, each being similar to a corresponding one (or more than one) of the acquired angiograpies.

In an example, the input unit is configured to provide information relating to a geometrical configuration of an X-ray acquisition unit that was used to acquire the at least one 2D X-ray image, and wherein the transform of the 3D model of the body part comprises utilization of the information relating to the geometrical configuration of the X-ray acquisition unit.

In other words, information relating to the position of the x-ray source and detector in relation to the patient, such that the direction that the X-rays that passed through the body part is approximately known, can be used in order to position and orientate the 3D model in a corresponding position to the patient's body part such that the 2D projection of the 3D model will already closely resemble the 2D angiogram.

In an example, the transform of the 3D model of the body part comprises application of a scaling factor.

In other words, the model can be scaled to account for varying sizes of body parts between patients. For example, the size of hearts varies between patients.

In an example, the scaling factor comprises an affine scaling factor.

In other words, not only can the model of the body part be changed in size uniformly but it can be scaled differently across the model of the body part. In other words, a scaling factor could linearly increase across the model of the body part such that at one extreme of the model of the body part the body part is not changed in size, but at the other extreme of the model of the body part the body part has been changed in size. The intermediate parts of the model of the body part can then be linearly or non-linearly scaled between the two extremes.

In an example, the transform of the 3D model of the body part comprises translation of the 3D model of the body part.

In other words, an improved estimate for the position of the model in space (3 translational parameters) can be computed, and this can be corrected for its scale (1, 2 or possibly 3 parameters), and for a slight rotation (3 parameters), and/or a slight translation (3 parameters).

In an example, the transform of the 3D model of the body part comprises rotation of the 3D model of the body part.

In an example, the transform of the 3D model of the body part comprises a registration of the 2D projection of the 3D model of the body part to the 2D X-ray image data of the vascular structure.

The term "registration" relates to a transform of the 3D model of the body part such that the 2D projection of the 3D modelled vascular structure has a vessel tree that spatially corresponds to a vessel tree in the 2D X-ray image data of the vascular structure. In other words, the vascular structure in the 2D projection of the 3D modelled vascular structure is optimally similar to that of the 2D X-ray image data of the vascular structure, or in other words the vessels in both the real X-ray image and the synthetic modelled images are as similar as possible.

In an example, the processing unit is configured to enable a user to annotate the at least one 2D projection of the 3D modelled vascular structure associated with the transformed 3D model of the body part, and wherein the processing unit is configured to apply the annotation to the 3D modelled vascular structure of the 3D model of the body part.

In other words, a clinician is enabled to transparently and accurately fill in his findings. The clinician can choose which of the angiographic image (2D X-ray image)/2D diagram (2D projection of the 3D modelled vascular structure) couples he wishes to use to annotate the coronary tree. Editing one of the diagrams (to position a stenosis for instance) will update all of them (since they present all a specific view of the same object—the generic 3D model). Therefore, the clinician will be able to choose the views over which the different stenoses are best visible to fill the report.

In an example, the processing unit is configured to enable a user to select a reporting format for reporting the at least one 2D projection of the 3D modelled vascular structure associated with the transformed 3D model of the body part, and/or the 3D modelled vascular structure associated with the transformed 3D model of the body part and/or the transformed 3D model of the body part.

In other words, a clinician is enabled to select the format in which he wants to present that information in a report. A straightforward way is to export some of the angiography/reprojected 2D diagram couples into the report. This will allow a clinician that would read the report to intuitively and accurately understand the nature of the findings of the exam. The user will also be able to generate other graphics summarizing his findings in a more concise yet compact way. He could resort to a flattened schematic 2D diagram (the 2D projection of the 3D modelled vascular structure), or to a 3D tree (the 3D modelled vascular structure) that he rotates in a digital report.

In this manner, an easy way to annotate the coronary tree is provided.

In an example, the at least one 2D X-ray image comprises a plurality of images; wherein, the processing unit is configured to select a visible and distinct 2D X-ray image from the plurality of images.

According to a second aspect, there is provided a medical system for providing synthetic representation of a vascular structure, the system comprising:

an X-ray image acquisition unit;
an apparatus for providing a synthetic representation of the vascular structure according to any of the preceding examples and aspect; and
an output unit;

The X-ray image acquisition unit is configured to provide the at least one 2D X-ray image. The output unit is configured to output data representative of the at least one 2D X-ray image and is configured to output data representative of the 3D model of the body part.

By providing a medical system for providing a synthetic representation of a vascular structure a clinician is automatically provided with the required reporting information associated with the intervention. The clinician is provided with information regarding the names of the parts of the coronary tree of the patient, enabling full and accurate reporting of both an intervention that is to be conducted and reporting of an intervention that has been conducted. By providing a synthetic representation of a vascular structure, the clinician can easily in the future review the angiograms and understand their spatial context, and different clinicians can review the angiograms and be automatically provided with information relating to the vascular structure observed within the angiograms without having to interpret the images.

According to a third aspect, there is provided a method for providing a synthetic representation of a vascular structure, the method comprising:

a) providing at least one 2D X-ray image comprising 2D X-ray image data of a vascular structure of a patient's body part;

b) providing a 3D model of the body part, the 3D model comprising a 3D modelled vascular structure and wherein the 3D model of the body part is a generic model of the body part;

c) determining a 2D projection of the 3D model of the body part, the 2D projection of the 3D model of the body part comprising a 2D projection of the 3D modelled vascular structure;

d) transforming the 3D model of the body part, wherein the transform of the 3D model of the body part comprises a determination of the pose of the 3D model of the body part such that a 2D projection of the 3D modelled vascular structure associated with the transformed 3D model of the body part is representative of the 2D X-ray image data of the vascular structure of the patient's body part; and e) generating a medical report based on information determined from the 3D model.

According to another aspect, there is provided a computer program element controlling apparatus as previously described which, in the computer program element is executed by processing unit, is adapted to perform the method steps as previously described. According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
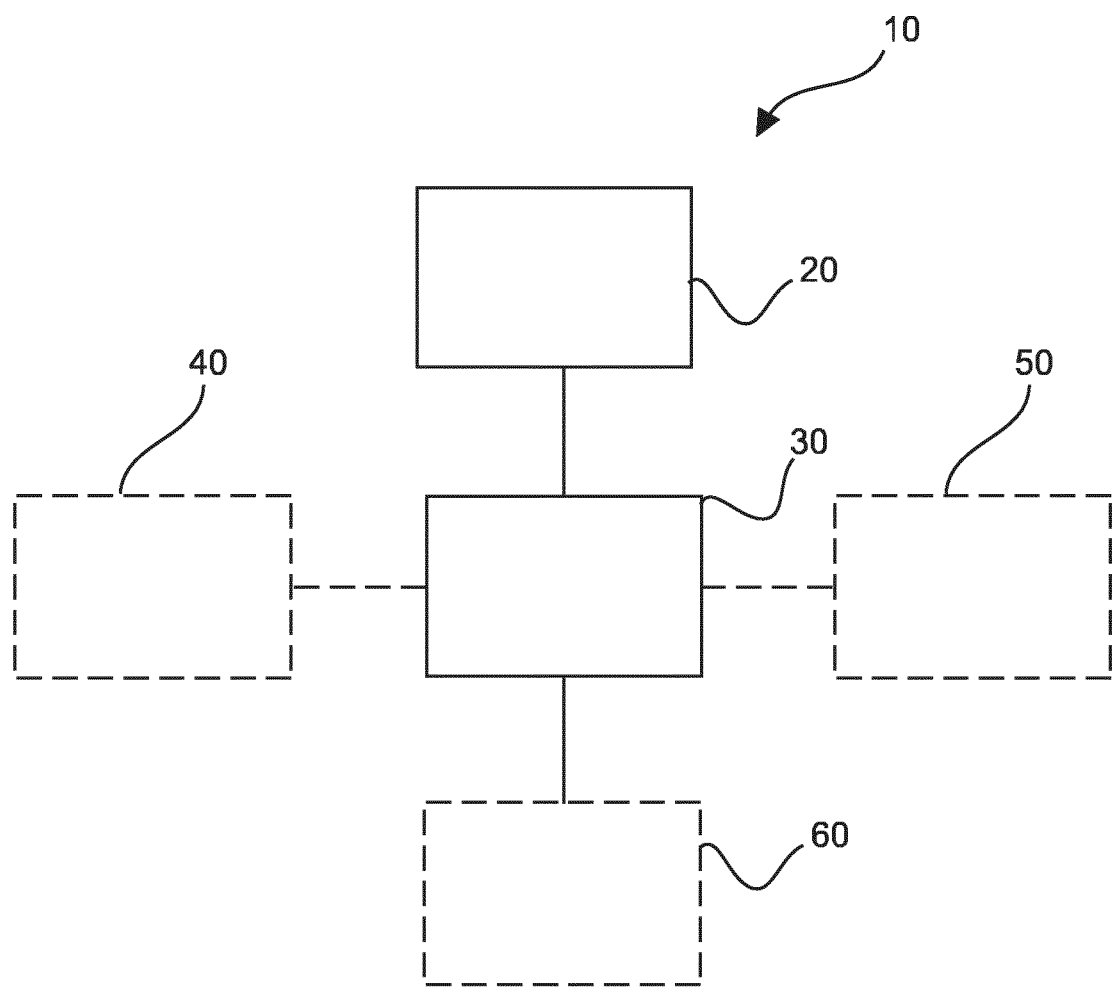
FIG. 1 shows a schematic set up of example of an apparatus for providing a synthetic representation of a vascular structure.

FIG. 1 shows an example of an apparatus 10 for providing a synthetic representation of a vascular structure. The apparatus comprises an input unit 20 and a processing unit 30. The input unit 20 is configured to provide at least one 2D X-ray image comprising 2D X-ray image data of a vascular structure of a patient's body part to the processing unit 30. The input unit 20 is also configured to provide a 3D model of the body part, the 3D model comprising a 3D modelled vascular structure to the processing unit 30. The processing unit 30 is configured to determine a 2D projection of the 3D model of the body part, the 2D projection of the 3D model of the body part comprising a 2D projection of the 3D modelled vascular structure. The processing unit 30 is also configured to transform the 3D model of the body part, wherein the transform of the 3D model of the body part comprises a determination of the pose of the 3D model of the body part such that a 2D projection of the 3D modelled vascular structure associated with the transformed 3D model of the body part is representative of the 2D X-ray image data of the vascular structure of the patient's body part. The processing unit 30 is further configured to generate a medical report based on information determined from the 3D model.

In an example, determining the pose comprises a refinement of the pose. In an example, the 3D vascular structure in the 3D model is known, i.e., all (or at least some) of the component parts of the vascular tree are known and can be named (annotated). In an example, the processing unit is configured to determine the 2D projection of the 3D model of the body part through the use of an image processing unit. In an example, the processing unit is configured to transform the 3D model of the body part through the use of an image processing unit.

In an example, the transform comprises the processing unit being configured to align at least one part of the vascular structure in the 2D X-ray image data with a corresponding at least one part of the vascular structure in the 2D projection of the 3D model vascular structure. For example, a position in the 2D projection of the 3D modelled vascular structure is translated into a position into the corresponding angiographic image—for example, alignment proceeds on the basis of very specific points of the vasculature (the main trifurcation for instance). In an example, at least some features (e.g. A, B, C) in the 2D projection of the 3D modelled vascular structure are aligned with or projected onto at least some similar features (e.g. A', B', C') in the at least one 2D X-ray image (angiogram). In an example, the aligning may comprise a region of the 2D projection of the 3D modelled vascular structure being placed over the top of the equivalent region of the at least one 2D X-ray image (angiogram), for example where a broad region is considered (a large segment for instance), and a blurry or very blurry version of the image is used as a reference. The alignment may be coarse or very coarse, however in examples this is good enough for the purpose of presenting the projection of the model in a visually equivalent configuration to the image.

In an example, refinement of the 3D model leads to a 2D projection of the 3D modelled vascular structure that more closely correlates with the 2D X-ray image data of the vascular structure than a pre-refinement 2D projection of the 3D modelled vascular structure does to the 2D X-ray image data of the vascular structure.

In other words, the pose of the 3-D model is determined (and in an example refined) so that the 3D model's 2D projection corresponds as much as possible to the actually observed injected coronary tree in the angiogram (2D X-ray image data of the vascular structure).

In an example, determination (and in an example refinement) comprises a rotation in space and/or a translation in space and/or application of a scaling factor to increase or decrease the size of the 3D model to account for variability in the size of the heart in patients. In other words, the spatial position and orientation of the 3D model is varied until its projection in two dimensions most closely matches the actually observed injected coronary tree in the acquired angiogram.

According to an example, the input unit is configured to provide the processing unit with information relating to a geometrical configuration of an X-ray acquisition unit 40 that was used to acquire the at least one 2D X-ray image, and wherein the transform of the 3D model of the body part comprises utilization of the information relating to the geometrical configuration of the X-ray acquisition unit.

In an example, information relating to the geometrical configuration comprises angulation and source to image distance SID of the X-ray acquisition unit. In an example, the 3-D model is initially positioned at the isocentre, for example according to the C-arm geometry.

According to an example, the transform of the 3D model of the body part comprises application of a scaling factor.

According to an example, the scaling factor comprises an affine scaling factor.

According to an example, the transform of the 3D model of the body part comprises translation of the 3D model of the body part.

In an example, the transform comprises a transformation, such that for example a translation along an x, y, or z axis can also incorporate a stretch or shrinking of a length element. In an example, the translation comprises any one, any two, or all three of translation along an x, y, or z axis. In an example, the transformation comprises an affine transformation, transforming all 9 parameters relating to translation, rotation and scaling, and other transformation that cannot be explained as a series of translations, rotations and scaling as would be appreciated by the skilled person's understanding of an affine transformation.

According to an example, the transform of the 3D model of the body part comprises rotation of the 3D model of the body part.

In other words, in an example the transform can comprise use of the geometrical information of the X-ray acquisition unit to provide for an initial orientation of the 3D model, followed by a change is scaling factor, followed by a translation of the model, followed by a rotation (or orientation) refinement to result in the correct determination of the pose of the 3D model, such that the 2D projection of the 3D modelled vascular structure correlates with the 2D X-ray image data of the vascular structure.

In an example, the rotation comprises any one, any two, or all three of rotation around an x, y, or z axis.

According to an example, the transform of the 3D model of the body part comprises a registration of the 2D projection of the 3D model of the body part to the 2D X-ray image data of the vascular structure.

In an example, registration of the 2D projection of the 3D model of the body part comprises registration of the 2D projection of the 3D modelled vascular structure to the 2D X-ray image data of the vascular structure.

Information relating to the matching of the 2D projection of the model to an angiogram can be found in the following paper "Projection.based motion compensation and reconstruction of coronary segments and cardiac implantable devices using rotational X-ray angiography", Gert Schoonenberg, Raoul Florent, Pierre Lelong, Onno Wink, Daniel Ruijters, John Carroll, Bart ter Haar Romeny, Medical Image Analysis, Volume 13, Issue 5, October 2009, pages 785-792.

In an example, registration of the 2D projection of the 3D model of the body part to the 2D X-ray image data of the vascular structure comprises progressively affining the 3D position of the 3D model so that the 2-D projection of the 3-D modelled vascular structure matches the coronary tree, as it is observed on the 2-D x-ray image (angiogram), as well as possible.

In an example, affining comprises defining an energy function that characterises how well the current 2-D projection of the 3-D modelled vascular structure matches the coronary tree in the angiogram. In an example, defining an energy function comprises computing a vessel energy map by filtering the angiogram, and sum the vessel energy overlapped to the 2-D projection of the 3-D modelled vascular structure. If the pose of the 3-D model is such that the 2-D projection of the 3-D modelled vascular structure corresponds well to the vessels in the angiogram, the energy will be high, if however the pose of the 3-D model does not lead to a correctly orientated 3-D model, there will be no such correspondence and the energy be low.

In an example, all possible poses, with a sampling step between poses, are investigated with associated 2-D projection of the 3-D model vascular structure being generated, and the one giving the highest energy corresponds to the 3-D model having the best pose.

In an example, the energy is differentiable with respect to the pose parameters (translations, rotations and scales), wherein the energy derivatives indicate the direction the pose parameters should be adapted in order to improve the alignment. In other words, a gradient descent will lead quickly to a (locally) optimal choice of the pose. In this manner, the required pose can be determined more quickly than for the case where all possible poses are investigated.

In an example, the vessel energy map is adapted through the application of Gaussian filtering. In this manner, this simple adaptation blurs the energy map, in order that the appropriate pose can be more easily determined. In this manner, a 3D model that does not accurately represent the real 3D coronary tree of a specific patient can be utilised.

Computation of a vessel energy map is described for example in the paper: "Improved vessel enhancement for fully automatic coronary modelling". V. Auvray, U. Jandt, R. Florent, D. Schäfer. SPIE Medical imaging 2009.

In an example, registration of the 2D projection of the 3D model of the body part to the 2D X-ray image data of the vascular structure comprises identifying some specific points (for instance branching points) in the angiogram by pure 2-D image processing. These points then service anchors to set the pose parameters for the 3-D model, so that the specific points in the 2-D projection of the 3-D modelled vascular structure match the corresponding specific points in the angiogram. In other words, a specific method is designed to align the 3-D model and the angiogram. An example of a specific method to identify such branching points is described in the paper: "Model-based segmentation of the left main coronary bifurcation from 2D angiograms", R. Lacroix, R. Florent, V. Auvray, ISBI 2012.

In an example, the apparatus comprises an output unit, wherein, the output unit is configured to output data representative of the at least one 2D X-ray image and is configured to output data representative of the 2D projection of the 3D modelled vascular structure associated with the transformed 3D model of the body part.

According to an example, the processing unit is configured to enable a user to annotate the at least one 2D projection of the 3D modelled vascular structure associated with the transformed 3D model of the body part, and wherein the processing unit is configured to apply the annotation to the 3D modelled vascular structure of the 3D model of the body part.

In an example, an annotation unit 50 or annotation module 50 is configured to enable a user to annotate the at least one 2D projection of the 3D modelled vascular structure associated with the transformed 3D model of the body part, and wherein the processing unit or the annotation unit or annotation module is configured to apply the annotation to the 3D modelled vascular structure of the 3D model of the body part.

According to an example, the processing unit is configured to enable a user to select a reporting format for reporting the at least one 2D projection of the 3D modelled vascular structure associated with the transformed 3D model of the body part, and/or the 3D modelled vascular structure associated with the transformed 3D model of the body part and/or the transformed 3D model of the body part.

In an example, a reporting unit 60 or reporting module 60 is configured to enable a user to select a reporting format for reporting the at least one 2D X-ray image and/or the 2D projection of the 3D modelled vascular structure associated with the transformed 3D model of the body part, and/or the 3D modelled vascular structure associated with the transformed 3D model of the body part and/or the transformed 3D model of the body part.

In an example, the processing unit is configured to automatically rotate the 3D model with angiograms that are viewed, such that the 3D model is presented at the same angulation as that for the angiogram being viewed.

According to an example, the at least one 2D X-ray image comprises a plurality of images; wherein, the processing unit is configured to select a visible and distinct 2D X-ray image from the plurality of images.

In an example, contrast agent is present during the acquisition of the visible and distinct 2D X-ray image. For example, contrast agent has been injected into at least a part of the vascular structure in order to provide image data of the vascular structure in a visible and distinct manner. In an example, the processing unit is configured to select a well-injected image. In other words, in the visible and distinct (e.g. well-injected) image the injected arteries, for example coronary arteries, are nicely visible. The term "visible and distinct" with respect to the at least a part of the vascular structure relates to at least part of the vascular structure being presented such that the vascular structure can be located and/or identified and/or delineated, either manually or automatically. The imagery can be visible and distinct due to contrast agent having been injected into the vascular structure at the time of image acquisition, for example during X-ray angiography.

In an example, the clinician or user can choose in which format he wants his findings to be presented in a report. He could resort to some of the angiography/2D projected model annotated diagram couples, and/or generate compact schematic representations (flattened 2D diagram, editable 3D diagram in a digital report).

In an example, the at least one 2D X-ray image comprises a plurality of images; wherein, the processing unit is configured to select a first 2D X-ray image and a second 2D X-ray image from the plurality of images, wherein the processing unit is configured to select the second 2D X-ray image as an image that is a registered image with respect to the first 2D X-ray image.

The term "registered image" relates to selection of the second 2D X-ray image such that it is registered with respect to the first 2D X-ray image. For example, the first and second 2D X-ray images can be registered with respect to cardiac cycle, patient breathing, patient motion, or image zooming, or any combination thereof. In other words, the body part (for example the heart) will be expected to be in a similar state between the two images. This leads to a spatially corresponding vessel tree between the heart that resulted in the first 2D X-ray image and the heart that resulted in the second 2D X-ray image. In other words, the 2D X-ray images, which could relate to different angulations through the heart, are then optimally useable to enable the at least one parameter to be updated when confronting the 3D model with the 2D X-ray images of the vascular structure. As the 3D model can be a generic model, then there will be expected to be inaccuracies between the 3D model and the real patient coronary tree and as such, such registration is optional. Image zooming does not relate to the anatomical status of the observed structure, and in an example can relate to an imaging setting that can be accounted for. This provides for a simplification, because a 3D model of the heart does not then need to be dynamic, in terms of changing with cardiac cycle as X-ray images can be selected that relate to a fixed moment in time within a cardiac cycle.

Figure 2:
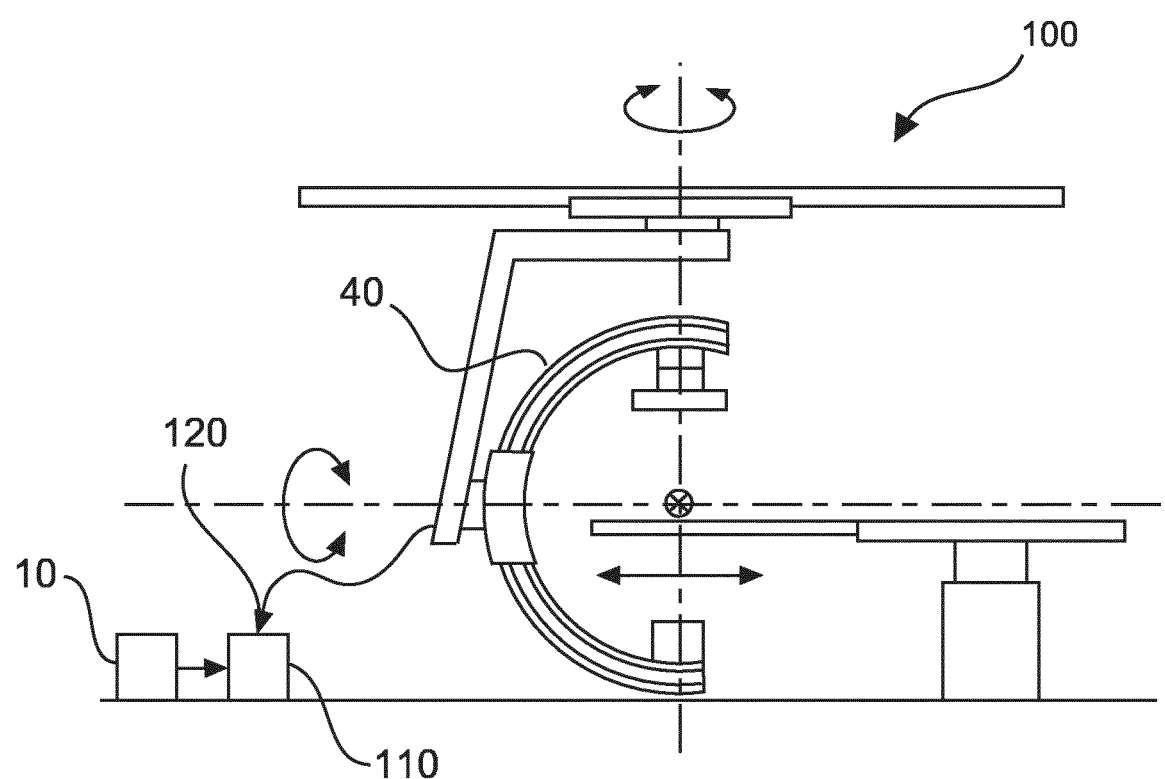
FIG. 2 shows a schematic set up of an example of a medical system for providing a synthetic representation of a vascular structure.

FIG. 2 shows an example of a medical system 100 for providing a synthetic representation of a vascular structure. The system comprises an X-ray image acquisition unit 40, an apparatus 10 for providing a synthetic representation of the vascular structure according to the above described FIG. 1, and an output unit 110. The X-ray image acquisition unit 40 is configured to provide the at least one 2D X-ray image to the apparatus 10 via communication cable 120. The apparatus 10 communicates with the output unit 10 via appropriate communication cabling and the output unit 10 is configured to output data representative of the at least one 2D X-ray image and is configured to output data representative of the 3D model of the body part.

In an example, the output unit is configured to output data representative of the 2D projection of the body part.

In an example, the output unit is configured to output data representative of the 2D projection of the 3D modelled vascular structure.

In an example, the output unit is configured to output the at least one 2-D X-ray image, and to output an image of the 2D projection of the 3D modelled vascular structure.

In an example, the X-ray image acquisition unit comprises an X-ray imaging device.

In an example, the X-ray image acquisition unit comprises a fluoroscopic imaging device. For example, a fluoroscopic low-dose x-ray device.

In an example, the X-ray image acquisition unit comprises an angiographic imaging device.

In an example, the output data is useable to enable a clinician to determine whether a vascular treatment or intervention was successful.

In an example, the system is used for Percutaneous Transluminal Coronary Angioplasty (PTCA) in catheter laboratories, to treat cardiac stenosis.

Figure 3:
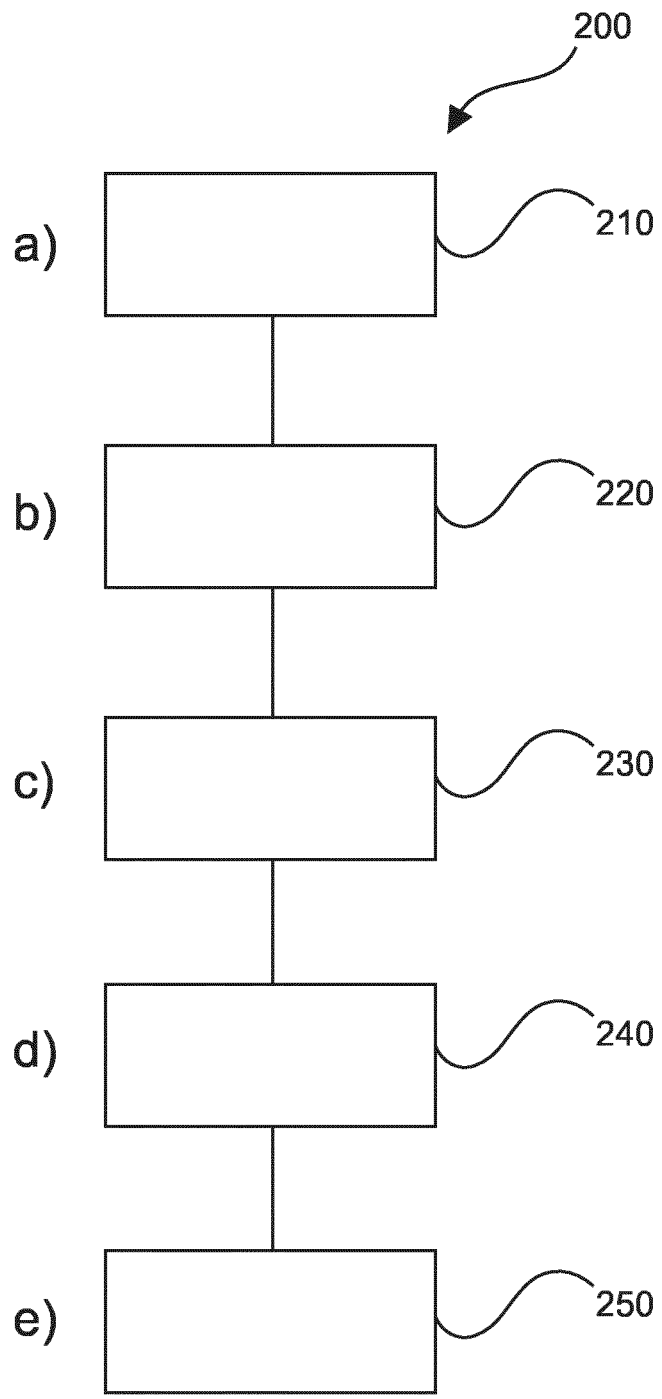
FIG. 3 shows an example of a method for providing a synthetic representation of a vascular structure.

FIG. 3 shows an example of a method 200 for providing a synthetic representation of a vascular structure in its basic steps. The method comprises the following:

In a first providing step 210, also referred to as step a), at least one 2D X-ray image comprising 2D X-ray image data of a vascular structure of a patient's body part is provided.

In a second providing step 220, also referred to as step b), a 3D model of the body part is provided, the 3D model comprising a 3D modelled vascular structure.

In a determining step 230, also referred to as step c), a 2D projection of the 3D model of the body part is determined, the 2D projection of the 3D model of the body part comprising a 2D projection of the 3D modelled vascular structure.

In a transforming step 240, also referred to as step d), the 3D model of the body part is transformed. The transform of the 3D model of the body part comprises a determination of the pose of the 3D model of the body part such that a 2D projection of the 3D modelled vascular structure associated with the transformed 3D model of the body part is representative of the 2D X-ray image data of the vascular structure of the patient's body part.

In a generating step 250, also referred to as step e), a medical report is generated based on information determined from the 3D model.

It is to be noted that steps 230 and 240 can performed together, and indeed step 230 can actually form a subpart of step 240.

In an example, determining the pose comprises a refinement of the pose.

In an example, the method comprises providing information relating to a geometrical configuration of an X-ray acquisition unit that was used to acquire the at least one 2D X-ray image, and transforming the 3D model of the body part comprises utilizing the information relating to the geometrical configuration of the X-ray acquisition unit.

In an example, transforming the 3D model of the body part comprises rotation of the 3D model of the body part. In an example, the rotation comprises any one, any two, or all three of rotation around an x, y, or z axis.

In an example, transforming the 3D model of the body part comprises translation of the 3D model of the body part. In an example, the translation comprises any one, any two, or all three of translation along an x, y, or z axis.

In an example, transforming the 3D model of the body part comprises a registration of the 2D projection of the 3D model of the body part to the 2D X-ray image data of the vascular structure.

In an example, the method comprises enabling a user to annotate the at least one 2D X-ray image and/or the 2D projection of the 3D modelled vascular structure associated with the transformed 3D model of the body part, and wherein the processing unit is configured to apply the annotation to the 3D modelled vascular structure of the 3D model of the body part.

In an example, the method comprises enabling a user to select a reporting format for reporting the at least one 2D X-ray image and/or the 2D projection of the 3D modelled vascular structure associated with the transformed 3D model of the body part, and/or the 3D modelled vascular structure associated with the transformed 3D model of the body part and/or the transformed 3D model of the body part.

In an example, the at least one 2D X-ray image comprises a plurality of images; wherein, the method comprises selecting a well injected 2D X-ray image from the plurality of images.

In an example, the at least one 2D X-ray image comprises a plurality of images; wherein, the method comprises selecting a first 2D X-ray image and a second 2D X-ray image from the plurality of images, wherein the second 2D X-ray image is selected as an image that is a registered image with respect to the first 2D X-ray image.

Examples of the apparatus and method for providing a synthetic representation of the vascular structure will now be described in more detail in conjunction with FIGS. 4-8.

Figure 4:
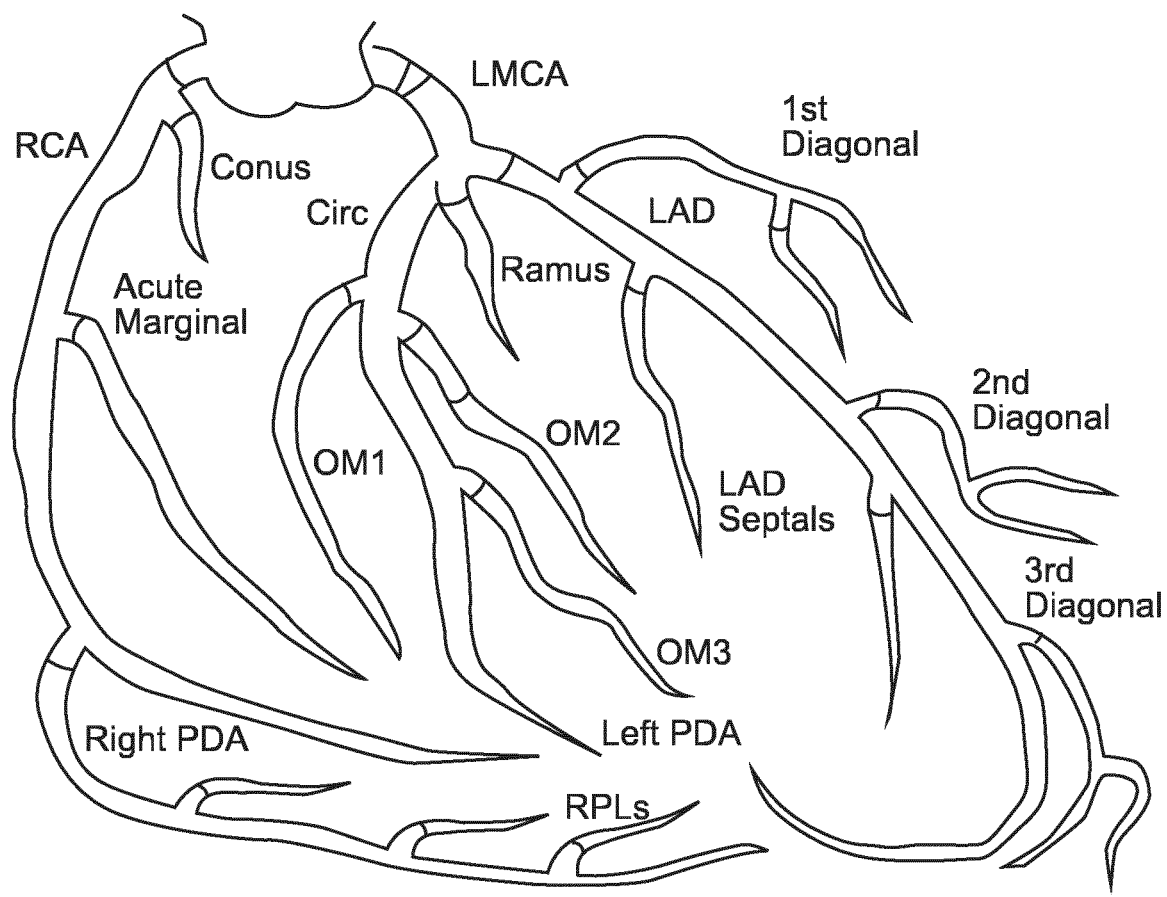
FIG. 4 shows an example of a flattened coronary diagram.
Figure 5:
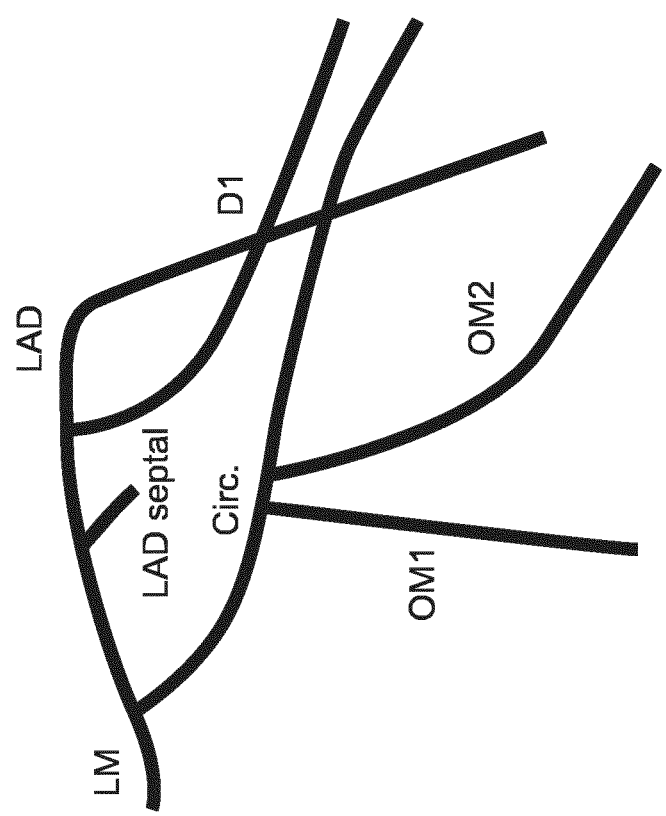
FIG. 5 shows an example image of a coronary angiography along with a 2D projection of a 3D modeled vascular structure from a similar perspective as that for the angiography.
Figure 5:
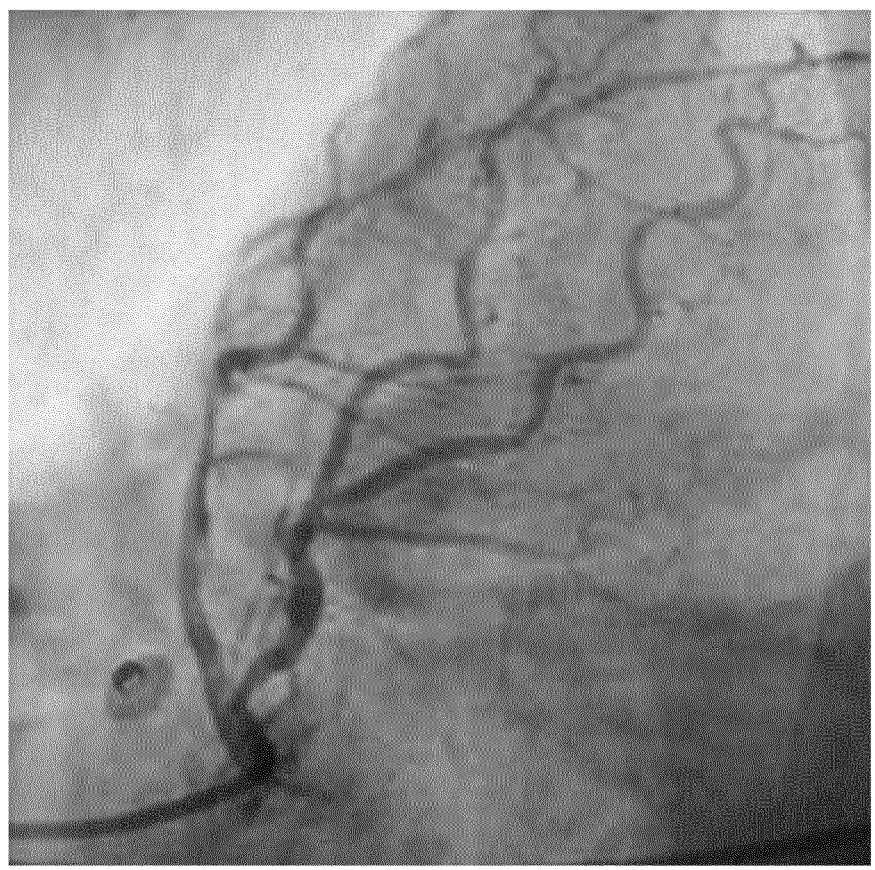
Figure 6:
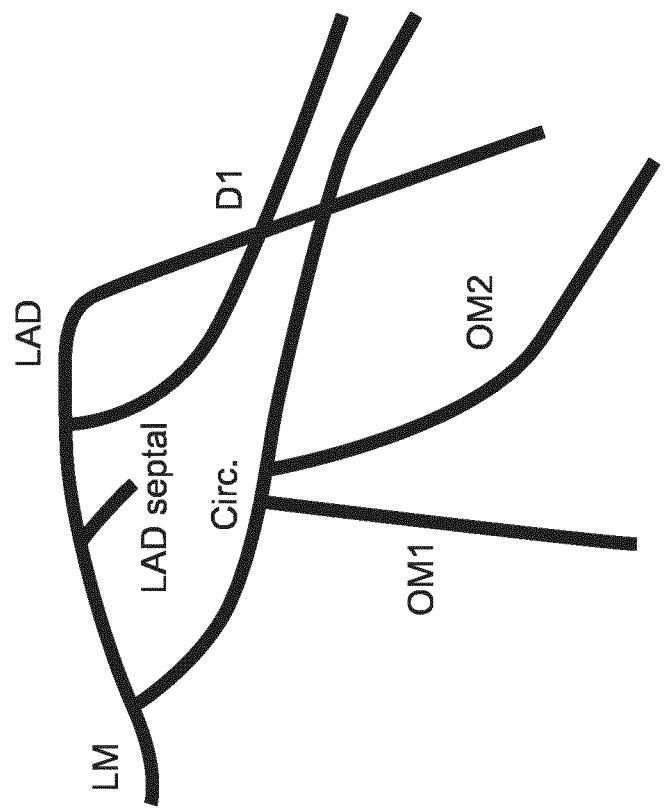
FIG. 6 shows the same information as presented in FIG. 5, but with the image replaced by a schematic diagram representation
Figure 6:
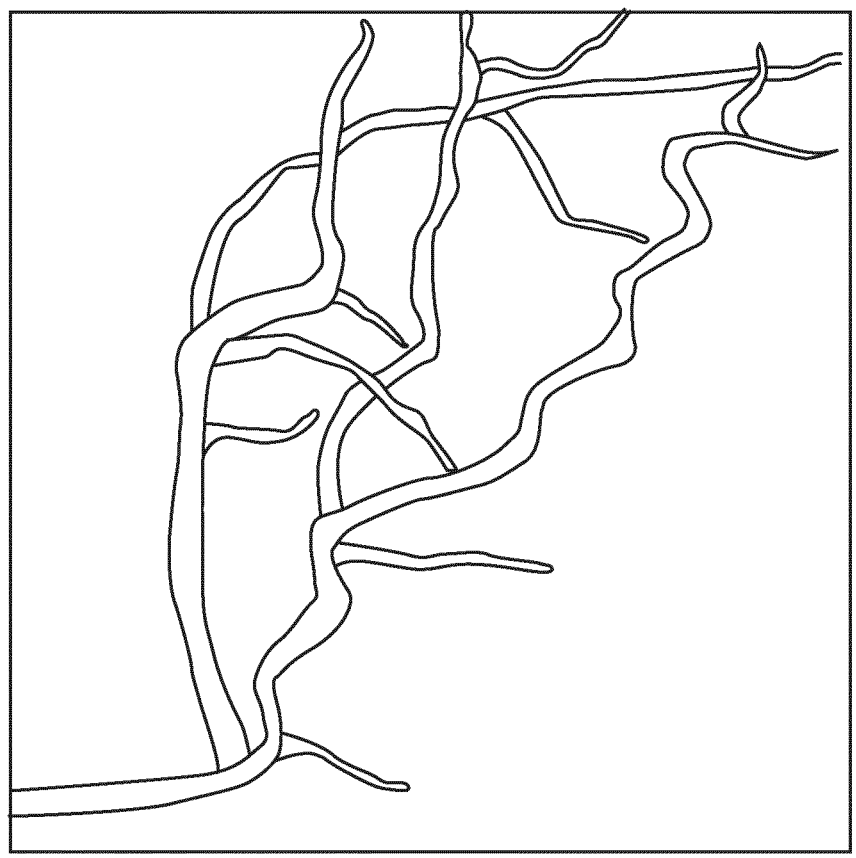

An issue being addressed is reviewed by reference to FIG. 4. FIG. 4 shows an example of a flattened coronary diagram. In order to be able to represent every possible coronary tree, the coronary diagram has to be very schematic. For example, the right and left coronary trees are flattened and presented side by side. The course of the secondary branches (marginal, septals, diagonals . . . ) is primarily dictated by the need to keep the diagram readable by voiding overlaps. This representation is by essence schematic, and therefore far from the actual structure and course of the arteries as observed on the angiographic images. As a result, it is not straightforward to relate such generic artery models with the observed angiographic images. Filling in the diagram requires an effort from the clinician while he mentally needs to project the injected vessels he observed on the exam sequences to an anatomical (semantic) model, and then back onto the generic diagram. Additionally, ambiguities can arise when a second clinician will perform the reverse task when he will need to read and understand the report, especially when a detailed understanding of the exact position of the stenosis will be needed.

The issue as outlined with reference to FIG. 4 can be addressed by associating each angiographic sequence with a diagram presenting the coronary tree from a similar perspective. Instead of displaying one artificially flattened complete 2D diagram, a complete 3D diagram of the vascular structure is utilised, which is reprojected into a series of 2D diagrams similar to the acquired angiographies. An example of the outcome of this is presented in FIGS. 5 and 6 which shows an example image of a coronary angiography along with a 2D projection of a 3D modeled vascular structure from a similar perspective as that for the angiography.

Figure 7:
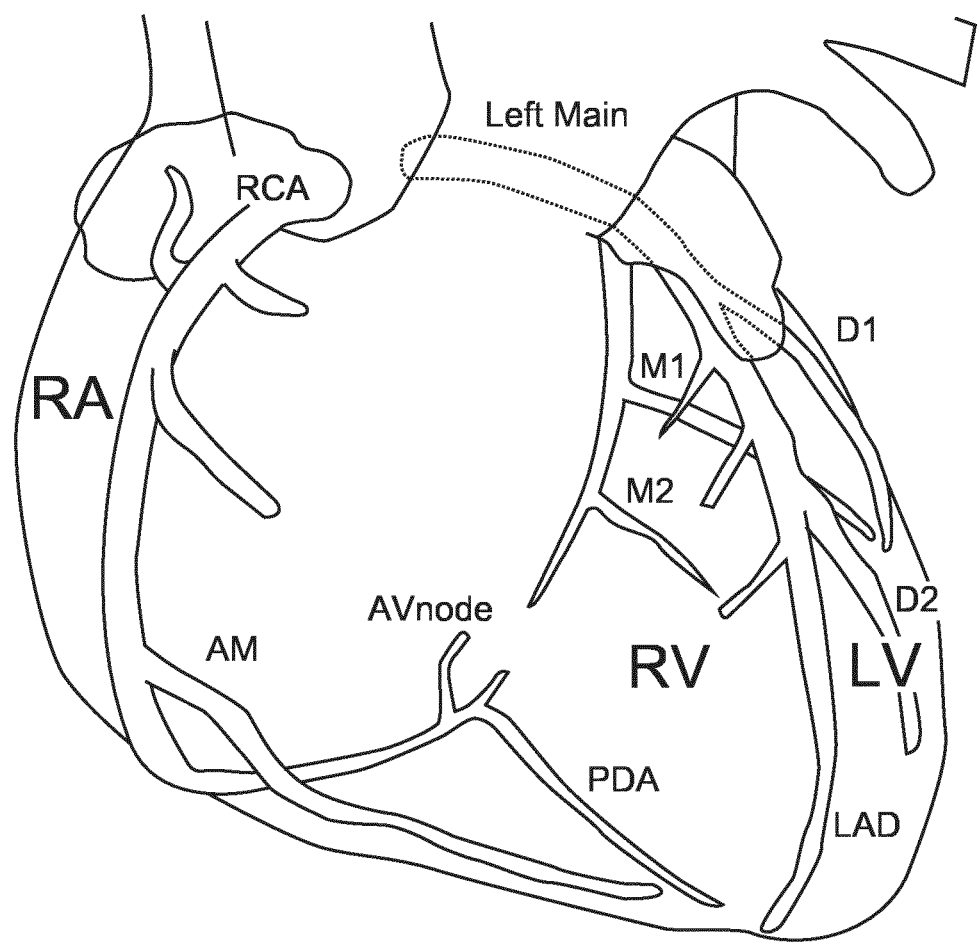
FIG. 7 shows an example of a 3D model of a body part.

In more detail, a 3D geometrical model of the coronary arteries is utilised. It decomposes the artery trees in the same anatomical segments as the 2D flattened model of FIG. 4. An example of a 3D model of a body part, in this example a heart, is shown in FIG. 7. More information on 3-D models body parts can be found in the following report: "Intrathoracic spatial location of specified coronary segments on the normal human heart. Applications in quantitative arteriography, assessment of regional risk and contraction, and anatomic display," J. T. Dodge Jr, B. G. Brown, E. L. Bolson, and H. T. Dodge, Circulation, vol. 78, no. 5, p. 1167, 1988.

Now, for each angiographic sequence:

One well injected image is automatically selected from the sequence (where the injected coronary arteries are nicely visible);

The 3D geometrical model is projected to produce a 2D representation, initially positioned at the isocenter, according to the C-arm geometry (defined by its angulation and its Source to image Distance SID);

The pose of the 3D geometrical model is refined so that it corresponds as much as possible to the actually observed injected coronary tree. In an example an improved estimate is computed for the position of the model in space (3 translational parameters), corrected for its scale (1, or possibly 3 parameters), and for a slight rotation (3 parameters).

An example of such a 3-D-2-D rigid registration can be found in the following paper: "Projection-based motion compensation and reconstruction of coronary segments and cardiac implantable devices using rotational X-ray angiography", Gert Schoonenberg, Raoul Florent, Pierre Lelong, Onno Wink, Daniel Ruijters, John Carroll, Bart ter Haar Romeny, Medical Image Analysis, Volume 13, Issue 5, October 2009, pages 785-792.

Starting from an initial pose (step 2), the method is to progressively affine the 3D model position so that its 2D reprojection matches the coronary tree, as it is observed on the 2D image (angiogram), as well as possible. This can be done by defining an energy function that details how well the current reprojected model matches the observed coronaries. For instance, a vessel energy map can be computed by filtering the observed image, and sum the vessel energy overlapped to the reprojected 3D model. If its pose corresponds well to the vessels, the energy will be high; if it is out of the vessels, the energy will be low. An example of computing a vessel energy map can be found in the following paper: "Improved vessel enhancement for fully automatic coronary modelling". V. Auvray, U. Jandt, R. Florent, D. Schäfer. SPIE Medical imaging 2009.

To get with certainty the best possible pose, all admissible transformations can be computed (translations, rotations and scales)—or at least a sampled version of it—and the one giving the highest energy is selected. Alternatively, the energy can be computed such that it is differentiable with respect to the pose parameters, so that the energy derivatives will indicate in which direction the pose parameters should be adapted in order to improve the alignment. In this way, a gradient descent will lead quickly to a (locally) optimal choice of the pose.

An adaptation is to blur the energy map (by Gaussian filtering), in order to translate any imprecision in the model (with respect to the true 3D coronary tree of the corresponding patient) into an imprecision on our matching criterion, in order to facilitate determination of the best possible pose.

Alternatively, a specific method to align the 3-D model and the angiogram can be designed, involving explicitly identifying some specific branching points in the angiogram by pure 2-D image processing. These few points will then serve as anchors to set the 3D model (so that the reprojected branching points match the ones extracted from the angiogram). An example of such an alignment method can be found in the following paper: "Model-based segmentation of the left main coronary bifurcation from 2D angiograms", R. Lacroix, R. Florent, V. Auvray, ISBI 2012.

Having aligned the acquired angiographies with a reprojected model, the model can then be exploited in two modules:

An annotation module, allowing the clinician to transparently and accurately fill in his findings.

The clinician can choose which of the angiographic image/2D diagram couples he wishes to use to annotate the coronary tree. Editing one of the diagrams (to position a stenosis for instance) will update all of them (since they present all a specific view of the same object—the generic 3D model).

The user can select the most relevant views to report his findings regarding the coronary tree.

Essentially, the user can select the views where the stenoses can be the most clearly seen (little foreshortening, little overlapping clutter) to accurately position them.

A reporting module, allowing the clinician to select the format in which he wants to present that information in the report.

Some of the angiography/reprojected 2D diagram couples can be exported into the report. This will allow a clinician that would read the report to intuitively and accurately understand the nature of the findings of the exam. In other words, this would have the additional benefit to help a second clinician, that would read this report, to understand faster and more accurately the findings of this exam;

The user will also be able to generate other graphics summarizing his findings in a more concise yet compact way.

He can resort to a 2D projection of the 3D modeled vascular structure, which has the advantage to present all information over one unique diagram, or He can resort to an annotated 3D tree that he rotate in a digital report.

In an example, the 3D modeled vascular structure in a digital report automatically rotates to the angulation of an angiogram that is referenced alongside the model, changing as different angiograms are viewed in the digital report along with the 3D model. In this manner, a clinician who consults the report can rotate it freely, helping him understanding the 3D geometry of these arteries, for instance in case of a follow-up examination.

Globally, the invention makes the diagram filling more transparent and less tedious, and allows for a smoother information transmission to other clinicians who would read the report afterwards.

Figure 8:
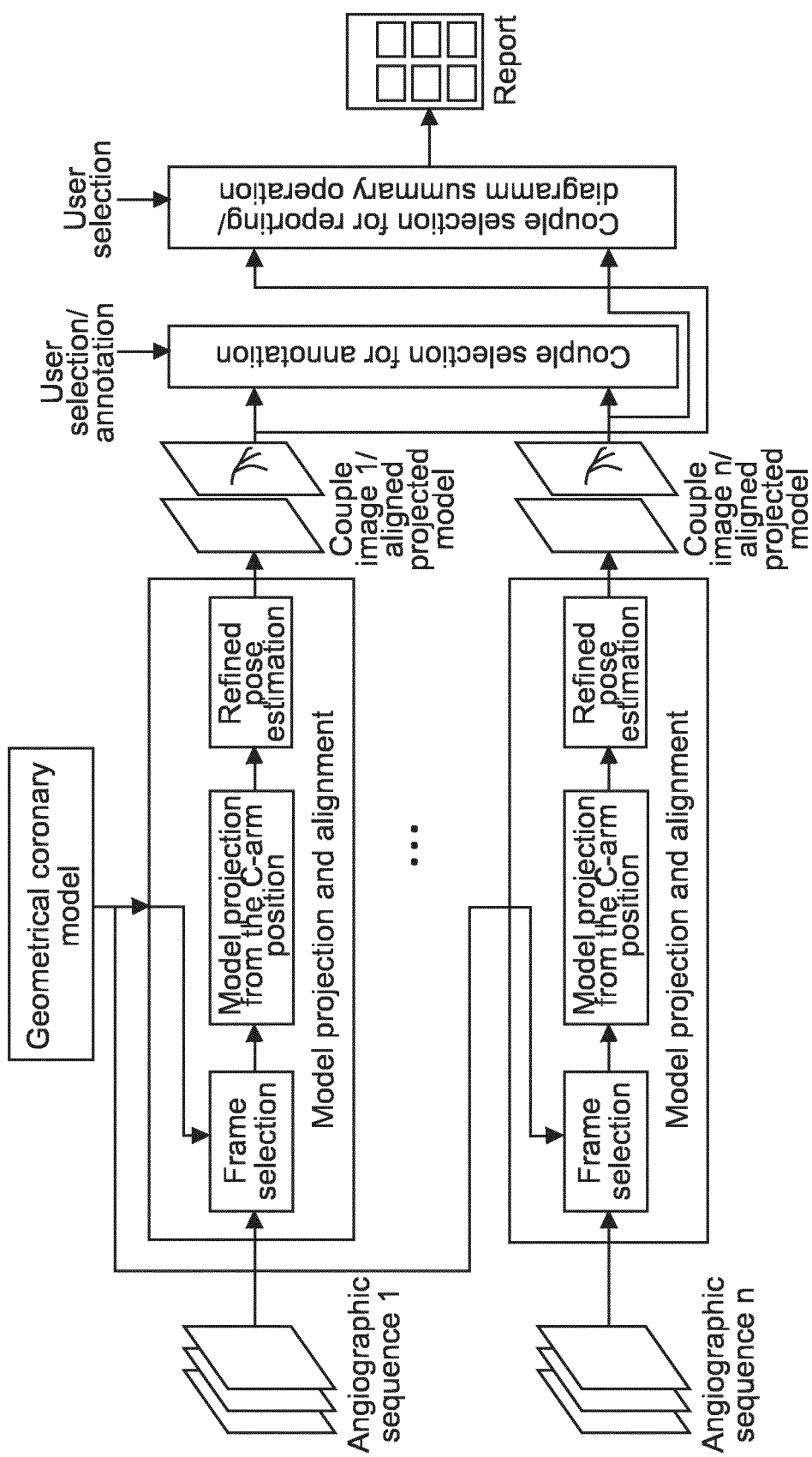
FIG. 8 shows an illustration of an example of a workflow of a method for providing a synthetic representation of a vascular structure.

FIG. 8 shows the above described method for providing a synthetic representation of a vascular structure as a detailed workflow.

In another exemplary embodiment, a computer program or computer program element is provided that is characterized by being configured to execute the method steps of the method according to one of the preceding embodiments, an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for providing a patient specific 3D model of a body part, the apparatus comprising:
   a memory that stores instructions; and
   a processing unit comprising a processor that executes the instructions, wherein, when executed by the processor, the instructions cause the processing unit to:
   provide at least one 2D X-ray image comprising 2D X-ray image data of a vascular structure of a patient's body part;
   provide a 3D model of the body part, the 3D model comprising a 3D modelled vascular structure, wherein at least one parameter commands an appearance of the 3D modelled vascular structure and wherein the 3D model is a generic model of the body part, the at least one parameter being related to one or more of a translation parameter, a rotation parameter and a scaling parameter;
   confront the 3D modelled vascular structure with the 2D X-ray image data of the vascular structure to determine the at least one parameter;
   update the 3D model as a function of the determined at least one parameter; and
   generate a medical report based on information determined from the 3D model.

2. The apparatus according to claim 1, wherein the processing unit is configured to determine a 2D projection of the 3D model of the body part, the 2D projection of the 3D model of the body part comprising a 2D projection of the 3D modelled vascular structure, and the processing unit is configured to adapt the at least one parameter such that a 2D projection of the adapted 3D modelled vascular structure is representative of the 2D X-ray image data of the vascular structure of the patient's body part; and wherein the adapted at least one parameter forms the determined at least one parameter.

3. The apparatus according to claim 2, wherein the processing unit is configured to modify the at least one parameter until the 2D projection of the modified 3D modelled vascular structure is representative of the at least 2D X-ray image data of the vascular structure, to adapt the at least one parameter.

4. The apparatus according to claim 2, wherein the processing unit is configured to transform the 3D model of the body part, wherein the transform of the 3D model of the body part comprises a determination of a pose of the 3D model of the body part.

5. The apparatus according to claim 4, further comprising an input unit configured to provide information relating to a geometrical configuration of an X-ray acquisition unit that was used to acquire the at least one 2D X-ray image, and wherein the transformed 3D model of the body part comprises utilization of the information relating to the geometrical configuration of the X-ray acquisition unit.

6. The apparatus according to claim 2, wherein the processing unit is configured to enable a user to annotate the 2D projection of the 3D modelled vascular structure associated with the transformed 3D model of the body part, and wherein the processing unit is configured to apply the annotation to the 3D modelled vascular structure of the 3D model of the body part.

7. The apparatus according to claim 2, wherein the processing unit is configured to enable a user to select a reporting format for reporting the 2D projection of the 3D modelled vascular structure associated with the transformed 3D model of the body part, and/or the 3D modelled vascular structure associated with the transformed 3D model of the body part and/or the transformed 3D model of the body part.

8. The apparatus according to claim 1, wherein the processing unit is configured to indicate at least one segment of the vascular structure in the at least one 2D X-ray image of the vascular structure and perform at least one measurement on the at least one segment and associate the at least one segment of the vascular structure in the at least one 2D X-ray image of the vascular structure with a corresponding at least one segment of the 3D modelled vascular structure; wherein the processing unit is configured to adapt the at least one parameter as a function of the at least one measurement; and wherein the adapted at least one parameter forms the determined at least one parameter.

9. The apparatus according to claim 1, wherein the at least one 2D X-ray image comprises a plurality of images; and wherein, the processing unit is configured to select a well injected 2D X-ray image from the plurality of images.

10. The apparatus according to claim 1, wherein an X-ray acquisition unit that was used to acquire the at least one 2D X-ray image was static at a time the at least one 2D X-ray image was acquired.

11. A medical system for providing a patient specific 3D model of a body part, the medical system comprising:
an X-ray image acquisition unit;
an apparatus for providing a patient specific 3D model of a body part according to any of the preceding claims;
a memory that stores instructions;
a processing unit comprising a processor that executes the instructions, wherein, when executed by the processor, the instructions cause the processing unit to: provide at least one 2D X-ray image comprising 2D X-ray image data of a vascular structure of a patient's body part; provide a 3D model of the body part, the 3D model comprising a 3D modelled vascular structure, wherein at least one parameter commands an appearance of the 3D modelled vascular structure and wherein the 3D model is a generic model of the body part, the at least one parameter being related to one or more of a translation parameter, a rotation parameter and a scaling parameter; confront the 3D modelled vascular structure with the 2D X-ray image data of the vascular structure to determine the at least one parameter; update the 3D model as a function of the determined at least one parameter; and generate a medical report based on information determined from the 3D model; and
an output unit.

12. The medical system according to claim 11, wherein the processing unit is configured to determine a 2D projection of the 3D model of the body part, the 2D projection of the 3D model of the body part comprising a 2D projection of the 3D modelled vascular structure, and the processing unit is configured to adapt the at least one parameter such that a 2D projection of the adapted 3D modelled vascular structure is representative of the 2D X-ray image data of the vascular structure of the patient's body part; and wherein the adapted at least one parameter forms the determined at least one parameter.

13. The medical system according to claim 12, wherein the processing unit is configured to modify the at least one parameter until the 2D projection of the modified 3D modelled vascular structure is representative of the at least 2D X-ray image data of the vascular structure, to adapt the at least one parameter.

14. The medical system according to claim 12, wherein the processing unit is configured to transform the 3D model of the body part, wherein the transformed 3D model of the body part comprises a determination of a pose of the 3D model of the body part.

15. The medical system according to claim 14, further comprising an input unit configured to provide information relating to a geometrical configuration of an X-ray acquisition unit that was used to acquire the at least one 2D X-ray image, and wherein the transform of the 3D model of the body part comprises utilization of the information relating to the geometrical configuration of the X-ray acquisition unit.

16. The medical system according to claim 12, wherein the processing unit is configured to enable a user to annotate the 2D projection of the 3D modelled vascular structure associated with the transformed 3D model of the body part, and wherein the processing unit is configured to apply the annotation to the 3D modelled vascular structure of the 3D model of the body part.

17. The medical system according to claim 12, wherein the processing unit is configured to enable a user to select a reporting format for reporting the 2D projection of the 3D modelled vascular structure associated with the transformed 3D model of the body part, and/or the 3D modelled vascular structure associated with the transformed 3D model of the body part and/or the transformed 3D model of the body part.

18. The medical system according to claim 11, wherein the processing unit is configured to indicate at least one segment of the vascular structure in the at least one 2D X-ray image of the vascular structure and perform at least one measurement on the at least one segment and associate the at least one segment of the vascular structure in the at least one 2D X-ray image of the vascular structure with a corresponding at least one segment of the 3D modelled vascular structure; wherein the processing unit is configured to adapt the at least one parameter as a function of the at least one measurement; and wherein the adapted at least one parameter forms the determined at least one parameter.

19. The medical system according to claim 11, wherein the at least one 2D X-ray image comprises a plurality of images; and wherein, the processing unit is configured to select a well injected 2D X-ray image from the plurality of images.

20. A tangible non-transitory computer readable storage medium that stores a computer program, the computer program, when executed by a processor, causing a medical system that includes the tangible non-transitory computer readable storage medium to perform a process of providing a patient specific 3D model of a body part, the process comprising:
providing at least one 2D X-ray image comprising 2D X-ray image data of a vascular structure of a patient's body part;
providing a 3D model of the body part, the 3D model comprising a 3D modelled vascular structure, wherein at least one parameter commands an appearance of the 3D modelled vascular structure and wherein the 3D model is a generic model of the body part, the at least one parameter being related to one or more of a translation parameter, a rotation parameter and a scaling parameter;

confronting the 3D modelled vascular structure with the 2D X-ray image data of the vascular structure to determine the at least one parameter;

updating the 3D model as a function of the determined at least one parameter; and generating a medical report based on information determined from the 3D model.

* * * * *